US011160910B2

(12) United States Patent
Madden et al.

(10) Patent No.: US 11,160,910 B2
(45) Date of Patent: Nov. 2, 2021

(54) CASSETTE ANNUNCIATION

(71) Applicant: Alcon Inc., Fribourg (CH)

(72) Inventors: Sean Christopher Madden, Mission Viejo, CA (US); Conrad Sawicz, Lake Forest, CA (US); Ryan Makoto Takakawa, Aliso Viejo, CA (US)

(73) Assignee: Alcon Inc., Fribourg (CH)

( * ) Notice: Subject to any disclaimer, the term of this patent is extended or adjusted under 35 U.S.C. 154(b) by 254 days.

(21) Appl. No.: 16/218,964

(22) Filed: Dec. 13, 2018

(65) Prior Publication Data

US 2019/0184072 A1 Jun. 20, 2019

Related U.S. Application Data

(60) Provisional application No. 62/599,932, filed on Dec. 18, 2017.

(51) Int. Cl.
*A61M 1/00* (2006.01)
*A61M 5/142* (2006.01)
*F04B 43/12* (2006.01)

(52) U.S. Cl.
CPC ...... *A61M 1/0058* (2013.01); *A61M 5/14228* (2013.01); *A61M 5/14232* (2013.01); *F04B 43/12* (2013.01); *A61M 2205/123* (2013.01); *A61M 2205/3306* (2013.01); *A61M 2205/3379* (2013.01); *A61M 2205/3389* (2013.01); *A61M 2205/502* (2013.01); *A61M 2205/587* (2013.01); *F04B 43/1269* (2013.01)

(58) Field of Classification Search
CPC ........ A61M 1/00; A61M 1/0058; A61M 1/14; A61M 1/28; A61M 1/30; A61M 1/301; A61M 1/3624; A61M 1/3621; A61M 2039/1094; A61M 2205/12; A61M 2205/14; A61M 39/10; A61M 2205/121; A61M 2205/583; A61M 2205/584; A61M 2205/587; A61M 2205/6081
See application file for complete search history.

(56) References Cited

U.S. PATENT DOCUMENTS

| 5,417,246 A * | 5/1995 | Perkins | A61M 1/0031 137/870 |
| 2008/0082077 A1* | 4/2008 | Williams | A61M 1/0058 604/506 |
| 2008/0264413 A1* | 10/2008 | Doherty | A61M 39/1011 128/202.27 |
| 2009/0099552 A1* | 4/2009 | Levy | A61M 39/10 604/533 |
| 2011/0088694 A1* | 4/2011 | Tobia | G01F 23/64 128/204.23 |
| 2012/0180789 A1* | 7/2012 | Tobia | A61M 16/0051 128/203.12 |

(Continued)

*Primary Examiner* — Nilay J Shah

(57) ABSTRACT

A surgical console has a receptacle for receiving a surgical fluidics cassette. The receptacle has a light source that transmits light to light pipes in the surgical fluidics cassette. The light pipes transmit light to a light transmissive optical interface surrounded by an opaque frame in the surgical fluidics cassette. The opaque frame is located at a fluid level detection system in the cassette. The system illuminates fluidic connectors on the surgical fluidics cassette without interfering with the fluid level detection system of a surgical console.

8 Claims, 9 Drawing Sheets

(56) References Cited

U.S. PATENT DOCUMENTS

| | | | | |
|---|---|---|---|---|
| 2013/0144227 A1* | 6/2013 | Locke | ............... | A61M 1/0035 |
| | | | | 604/318 |
| 2013/0276780 A1* | 10/2013 | Tobia | ............... | A61M 16/0883 |
| | | | | 128/202.22 |
| 2014/0005573 A1* | 1/2014 | Burkett | ............... | A61B 5/6851 |
| | | | | 600/585 |
| 2014/0081224 A1* | 3/2014 | Gao | ............... | A61F 9/00736 |
| | | | | 604/319 |
| 2015/0040896 A1* | 2/2015 | Chodkowski | ....... | A61M 16/021 |
| | | | | 128/202.22 |
| 2017/0189231 A1* | 7/2017 | Baxter | ............... | A61M 1/00 |
| 2017/0209637 A1* | 7/2017 | Schaefer | ............... | A61M 1/367 |

* cited by examiner

CASSETTE ANNUNCIATION

PRIORITY CLAIM

This application claims the benefit of priority of U.S. Provisional Patent Application Ser. No. 62/598,653 titled "MULTIPLE-INPUT-COUPLED ILLUMINATED MULTI-SPOT LASER PROBE," filed on Dec. 14, 2017, whose inventors are Jochen Horn, Alireza Mirsepassi, and Ronald T. Smith, which is hereby incorporated by reference in its entirety as though fully and completely set forth herein.

BACKGROUND

Field of the Disclosure

The present disclosure relates to systems for illuminating fluidic connectors on a surgical fluidics cassette and, more specifically, to systems for illuminating fluidic connectors on a surgical fluidics cassette without interfering with a fluid level detection system.

Description of Related Art

Ophthalmic surgery is often conducted using a surgical console and a number of associated consumables such as surgical fluidics cassettes, fluid bags, tubing, hand piece tips and other consumables. A surgical fluidics cassette can provide a variety of functions depending on the procedure and surgical instrumentation. For example, surgical fluidics cassettes can help manage irrigation and aspiration flows into and out of a surgical site. Surgical fluidics cassettes can also provide support for fluid bags, a manifold for directing vacuum/pressure to surgical instrumentation, and other functionality. However, given the large number of fluidics connections on modern surgical fluidics cassettes, the setup of the fluidics connections can be confusing and onerous to a user.

A solution that has been applied to the electric connections of a surgical console involves presenting a graphical user interface to an operator that directs the operator to select an appropriate electric connector and illuminating a ring around each of the electric connection ports on the console to guide the operator to connect the appropriate electric connector to the appropriate port. However, since a surgical fluidics cassette is a consumable product, adding dedicated illumination to the fluidics ports of the cassette would be wasteful and unnecessarily add cost to the procedure. Also, a surgical console can include lights and light sensors to detect levels and pressure of the fluids contained in the surgical fluidics cassettes. Accordingly, additional light sources on the surgical console should not introduce light into areas of the sensors that would interfere with the detection of fluid levels and pressure.

SUMMARY

The disclosed embodiments of the present technology relate to systems for illuminating fluidic connectors on a surgical fluidics cassette and, more specifically, to systems for illuminating fluidic connectors on a surgical fluidics cassette without interfering with a fluid level detection system in a surgical console.

In particular embodiments, a surgical console can include a fluidics system including a cassette receiver having a pump and various pneumatic input and output ports that interface with surgical fluidics cassette. The cassette receiver can also include a fluid level detection system having light sources and sensors that, together, can detect a fluid level in one or more chambers of a surgical fluidics cassette coupled with the cassette receiver. The cassette receiver can also include a fluidic port illumination light source for transmitting illumination to transmissive surface portions of the cover of the surgical fluidics cassette to facilitate in the setup of the fluidics system. The fluidic port illumination light source can arranged within the cassette receiver such that, when the surgical fluidics cassette is coupled with the cassette receiver, the fluidic port illumination light source interfaces with a transmissive optical interface surrounded by an opaque frame on the surgical fluidics cassette. The opaque frame can prevent illumination light from the fluidic port illumination light source from interfering with the fluid level detection system. Likewise, the transmissive optical interface can allows the illumination light to transmit toward the transmissive surface portions of the cover of the surgical fluidics cassette.

In particular embodiments the surgical fluidics cassette can include fluid chambers containing a variable level of fluid, and the surgical fluidics cassette can be configured such that the fluid chambers align with the fluid level detection system in the cassette receiver. The surgical fluidics cassette can also include on its cover fluidic port connections for coupling fluidic accessories with the surgical fluidics cassette. The surgical fluidics cassette can also include an opaque substrate covering the fluidic port connections and including optically transmissive interface portions which allow access to the fluidic port connections and which include an optically transmissive material on the surface of the opaque substrate at least partially surrounding the fluidic port connections. The opaque substrate also includes light pipes coupled with the optically transmissive interface portions of the opaque substrate.

In particular embodiments, the surgical fluidics cassette can also include an opaque frame coupled to the cassette body for preventing a fluidic port illumination light from the fluidic port illumination light source from interfering with the light-sensitive fluid level detection system when the surgical fluidics cassette is coupled with the cassette receiver. The opaque frame can include a transmissive optical interface arranged to align with a fluidic port illumination light source in the cassette receiver. The transmissive optical interface can also align with the plurality of light pipes in the opaque substrate. The light pipes in the opaque substrate can connect the transmissive optical interface with the optically transmissive interface portions of the opaque substrate and allow the fluidic port illumination light to illuminate the transmissive interface portions to annunciate the fluidic port connections.

In particular embodiments, the surgical console can also include a processor, a controller, and a computer-readable medium containing instructions which, when executed by the processor, control the controller. The controller can selectively cause the fluidic port illumination light source to provide illumination to the transmissive optical interface of the surgical cassette, to the light pipes, and to the transmissive interface portions of the opaque substrate, thereby illuminating one or more of the transmissive interface portions. Also the processor can cause the display to display a graphical user interface (GUI) including visual instructions for connecting one or more fluidic accessories to the one or more of the plurality of fluidic port connections on the cassette.

In particular embodiments, the fluidic port illumination light source can selectively illuminate one or more of the transmissive interface portions individually or in combinations. For example, the fluidic port illumination light source can include an array of light sources, an array of light sources having varied colors, aiming light sources, field programmable light sources, etc. The controller can further selectively activate one or more of the illumination sources in the array of illumination sources and cause one or more of the transmissive interface portions to illuminate consistently with the visual instructions on the GUI.

BRIEF DESCRIPTION OF THE DRAWINGS

For a more complete understanding of the present technology, its features, and its advantages, reference is made to the following description, taken in conjunction with the accompanying drawings, in which.

DESCRIPTION

The technology described below involves a fluidic port illumination light source arranged within a cassette receiver of a surgical console, a surgical fluidics cassette with a plurality of transmissive portions surrounding one of a plurality of fluidic port connections of the cassette, and a system for preventing light from the fluidic port illumination light source from interfering with a fluid level detection system in the surgical console.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

Figure 1:
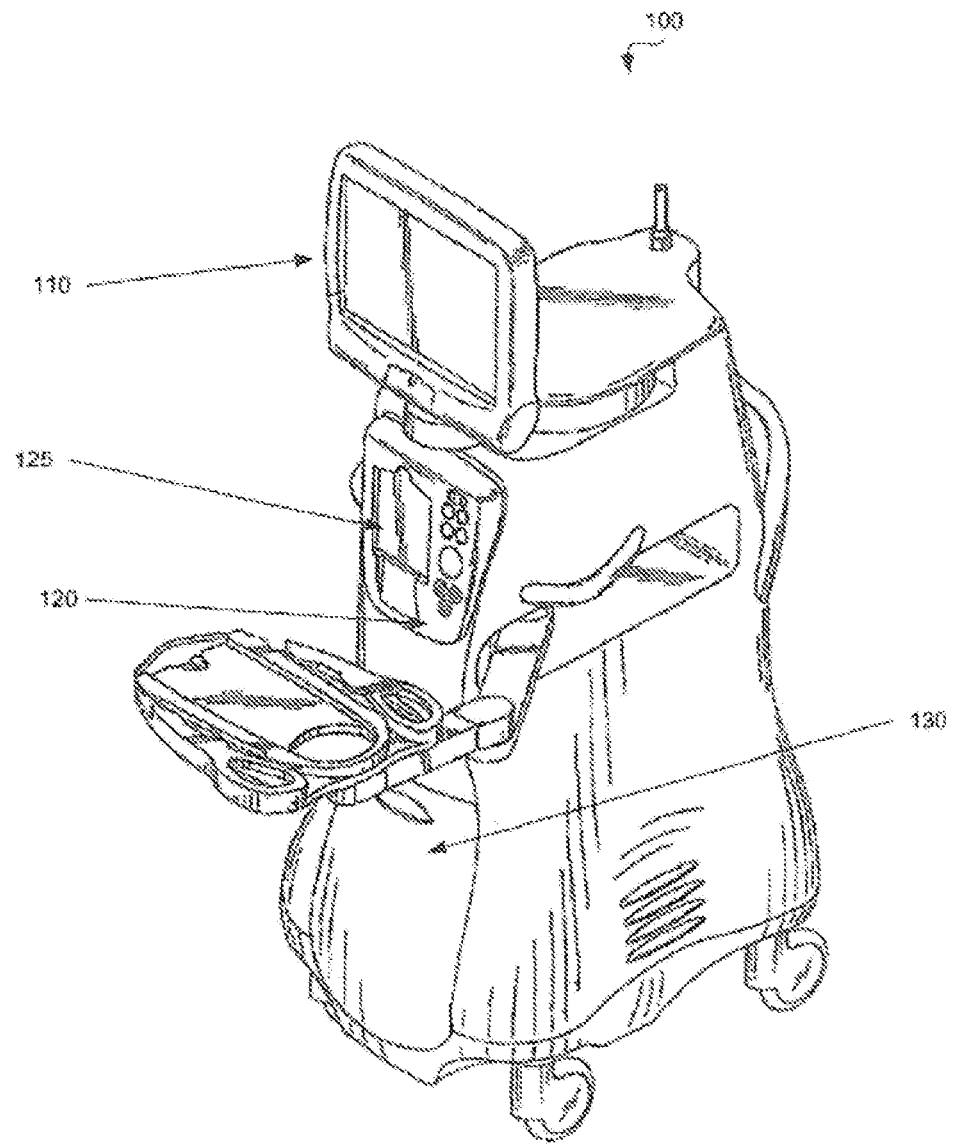
FIG. 1 is a diagrammatic representation of an ophthalmic surgical console according to a particular embodiment of the present disclosure.

FIG. 1 is a diagrammatic representation of a surgical console 100 according to one embodiment of the present disclosure. The surgical console 100 can include a connection panel 120 used to connect various tools and consumables to surgical console 100. Connection panel 120 can include, for example, a coagulation connector, connectors for various hand pieces, and a cassette receiver 125. In operation, a surgical fluidics cassette (not shown) can be placed in cassette receiver 125. A clamp in surgical console 100 clamps the surgical fluidics cassette in place to minimize movement of the surgical fluidics cassette during use. The clamp can clamp the top and bottom of the surgical fluidics cassette, the sides of the surgical fluidics cassette or otherwise clamp the surgical fluidics cassette.

The surgical console 100 can include a monitor 110 and a processor (not shown) for executing instructions for operating the various connected accessories and for displaying a graphical user interface (GUI) on the monitor 110. The surgical console 100 can also include a variety of user friendly features, such as a foot pedal control (e.g., stored behind panel 130) and other features.

Figure 2:
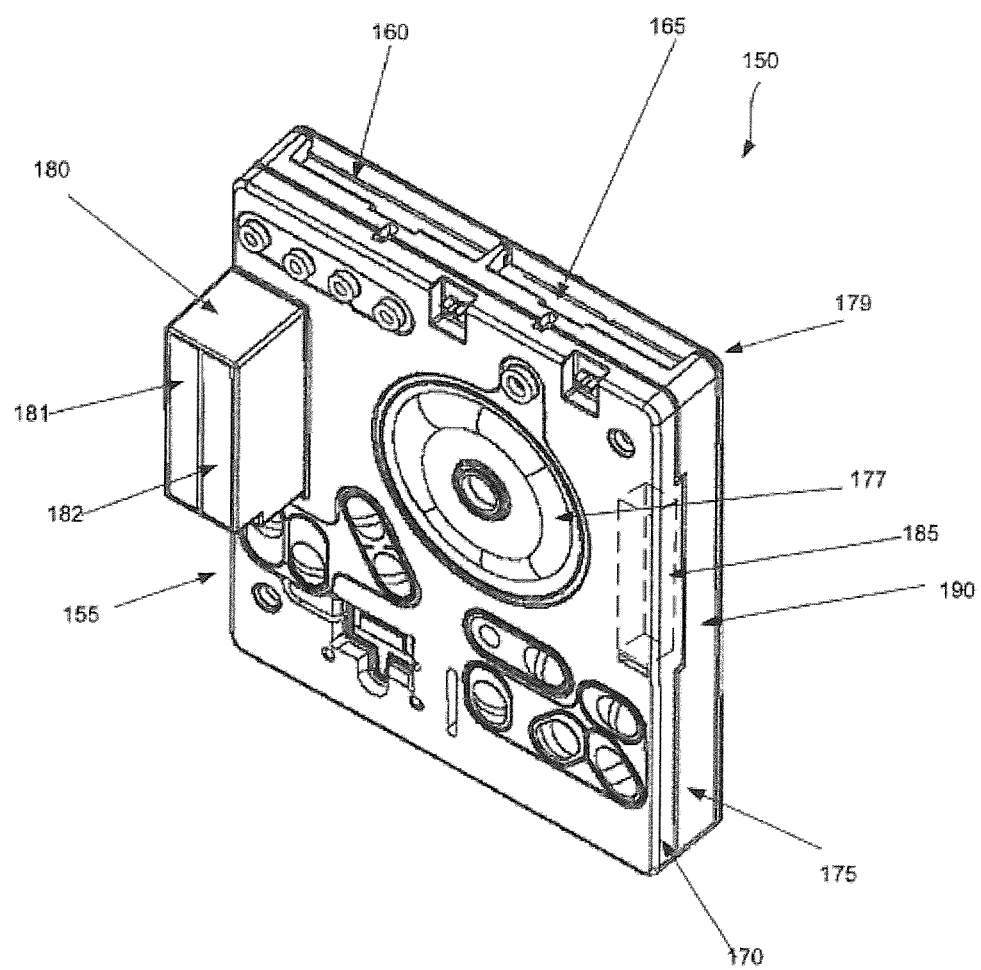
FIG. 2 illustrates a surgical fluidics cassette according to a particular embodiment of the present disclosure.

FIG. 2 illustrates an example of a surgical fluidics cassette 150 in accordance with a particular embodiment of the present disclosure. The surgical fluidics cassette 150 can provide a closed system fluidic device that can be discarded following a surgical procedure. The surgical fluidics cassette 150 can include a cassette body 155 and portions that interface with the clamp (e.g., indicated generally at clamping zones 160 and 165) projecting from the cassette body 155. Surgical fluidics cassette 150 can be formed of ABS plastic or other suitable material. In the embodiment shown, surgical fluidics cassette 150 is formed from three primary sections: an inner or surgical console interface section 170 that faces the surgical console when cassette 150 is inserted into surgical console 100, a middle section 175 and a cover plate 179. The various sections of surgical fluidics cassette 150 can be coupled together via a press fit, interlocking tabs, chemical bonding, thermal bonding, mechanical fasteners or other attachment mechanism known in the art. In other embodiments, surgical fluidics cassette 150 can be formed of a single piece or multiple pieces.

The surgical console interface section 170 of surgical fluidics cassette 150 can face the console during use and provide an interface for fluid flow channels (e.g., flow channel 177 for the peristaltic pump provided by an elastomeric pump membrane), valves (e.g., infusion/aspiration valves), and other features to manage fluid flow. The surgical fluidics cassette 150 can also attach to a fluid bag (not shown) to collect fluids during a procedure.

The surgical fluidics cassette 150 can also include chambers to hold fluids for aspiration and infusion. For example, chamber cartridge 180 can include two infusion chambers 181/182. A third chamber 185 can be internal to surgical fluidics cassette 150 on the opposite side of surgical fluidics cassette 150 from chamber cartridge 180 (e.g., at the side of surgical fluidics cassette 150 indicated by 190). In some embodiments, the level of fluid in the chambers 181/182/185 can be determined in a noninvasive manner. For example, as described below, light can be projected into the chamber walls using a vertical light source. Depending on the reflection or refraction of light at the chamber, a vertical sensor array will detect or not detect light at various points along the array's vertical axis. Based on the transition between illuminated and non-illuminated portions of the sensor array, the level of the fluid in the chamber can be detected.

Figure 3:
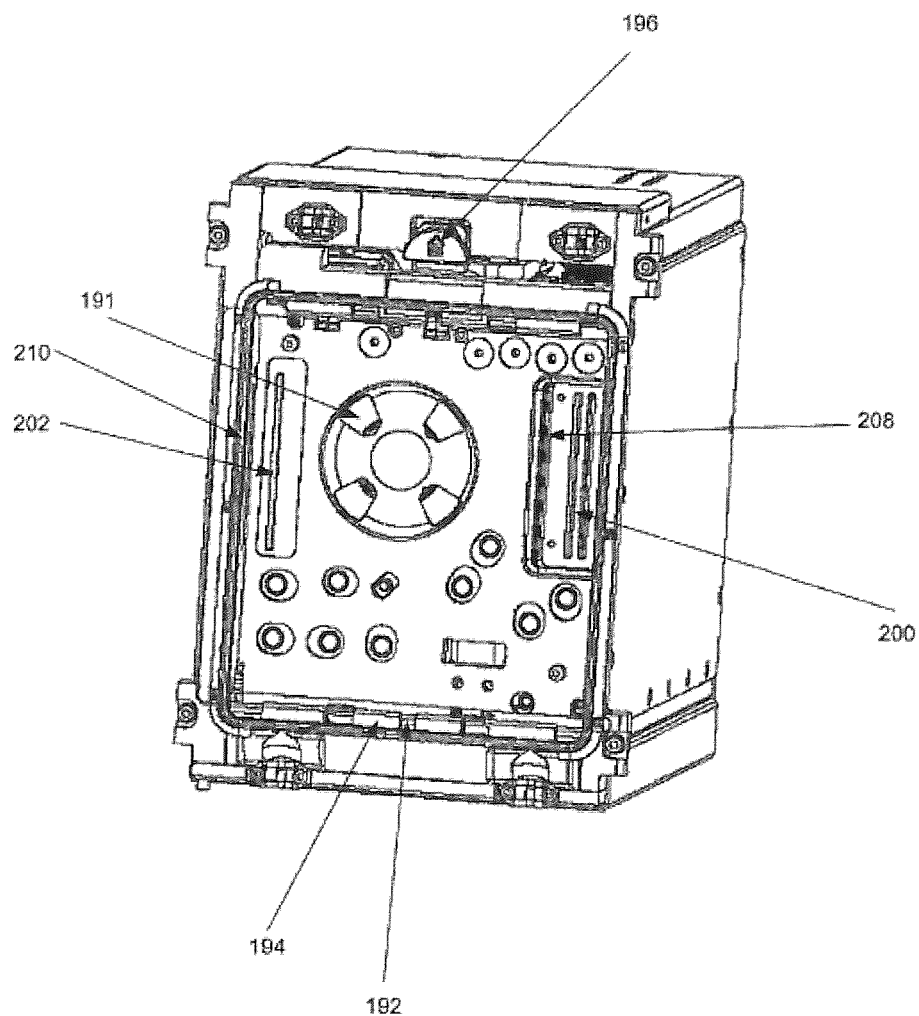
FIG. 3 is a diagrammatic representation of a cassette receiver, according to a particular embodiment of the present disclosure, without a surgical fluidics cassette inserted.

FIG. 3 is a diagrammatic representation of one embodiment of cassette receiver 125 without a surgical fluidics cassette inserted therein. Cassette receiver 125 can have various pneumatic input and output ports to interface with the surgical fluidics cassette. Cassette receiver 125 can further include an opening to allow peristaltic pump rollers 191 to contact the surgical fluidics cassette during operation. The surgical fluidics cassette is held in place by a clamp having a bottom rail 192 and a top rail (not shown). Each rail can have outer clamping fingers (e.g., clamp finger 194) that contact the surgical fluidics cassette in corresponding clamping zones and inner clamping fingers to locate the surgical fluidics cassette during insertion and push the surgical fluidics cassette out of cassette receiver during release. A release button 196 is pressed to initiate release of the surgical fluidics cassette from the clamp.

Also, the cassette receiver 125 can include linear light sources to project light into the walls of the cassette chambers (e.g., chambers 181/182/185 in FIG. 2) and sensor arrays to detect the light refracted through the chamber (or reflected from the chamber wall). Each linear light source can include a plurality of light sources vertically arranged (i.e., to project light along vertically spaced transmission paths) and positioned to project light into a wall of the cassette. For example, the linear light source 200 can project light into chambers 181/182 (FIG. 2). The linear light source 200 can contain a first set of light sources aligned to project light into chamber 181 and a second set of light sources arranged at a 90 degree angle (or other angle) from the first set of light sources to project light into chamber 182. Similarly, the linear light source 202 can project light into the walls of chamber 185 (FIG. 2). Respective linear sensor arrays can receive light refracted through the chamber or reflected at the chamber surface. For example, a sensor array located in wall 208 can receive light from light source 200 projected at chamber 182 and a sensor array in wall 210 can receive light from light source 202. Each sensor array can include vertically arranged portions to receive light through the wall of the cassette chamber. The vertically arranged portions can be, for example, digital camera sensing elements, separate sensors or other mechanisms for sensing illumination.

The linear light source 200 and linear sensor array can be connected to the processor which can use the light source data, the refractive indexes of the cassette surface, air and the fluid, the angle of the light, etc. to calculate the fluid levels. Stray light in proximity to the sensor array can interfere with the calculation of fluid levels; however, as noted above, illuminating the various ports on a surgical cassette can be helpful in setting up the surgical console.

Figure 4:
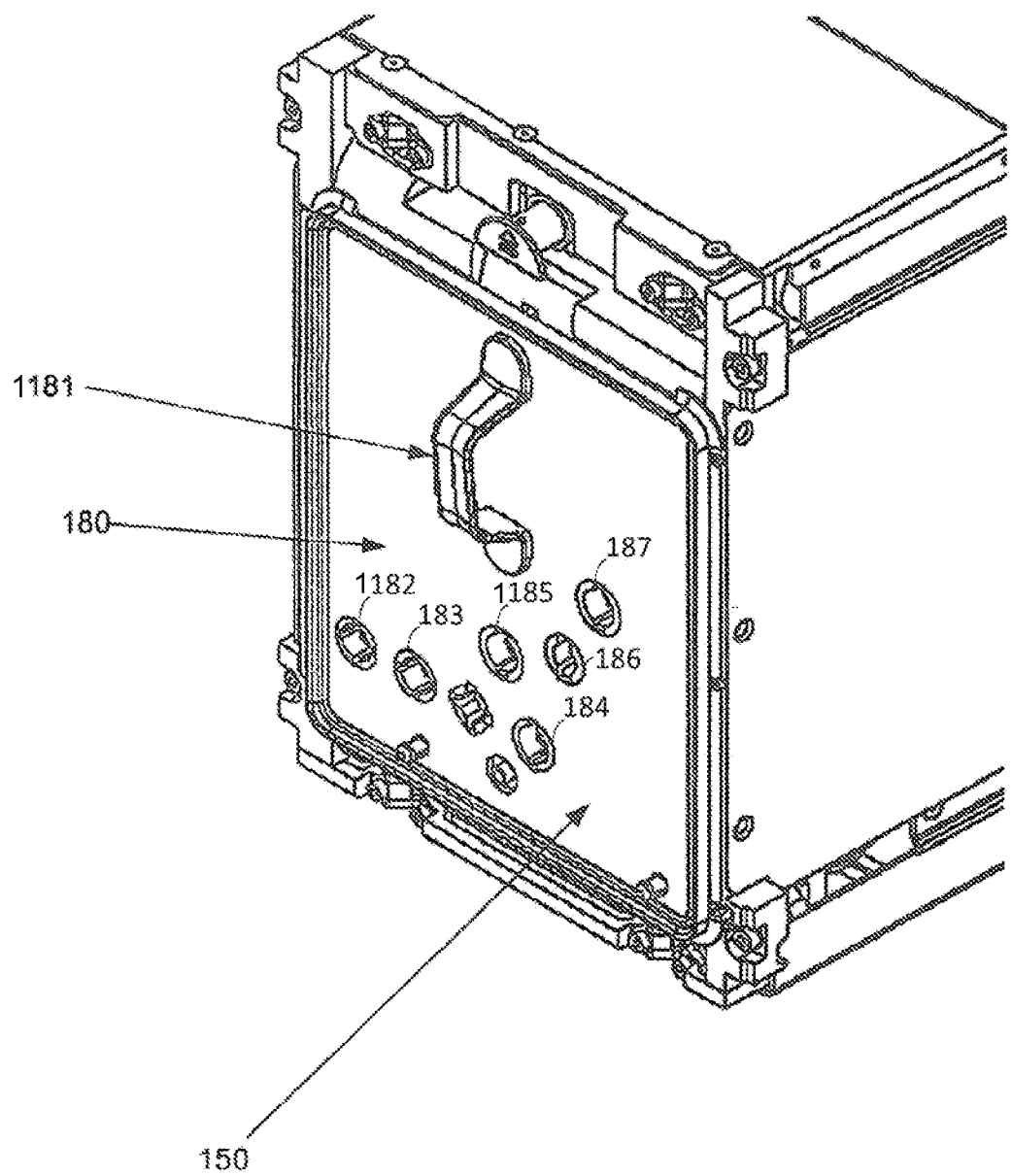
FIG. 4 is a diagrammatic representation of the surgical fluidics cassette of FIG. 23 inserted into the cassette receiver of FIG. 3.

As explained above, the setup of the fluidics connections on a surgical console can be confusing and onerous to a user given the large number of fluidics connections on the surgical fluidics cassette. FIG. 4 is a diagrammatic representation of surgical fluidics cassette 150 inserted in cassette receiver 125, with the surgical fluidics cassette including a front cover plate 180, a handle 1181, and a plurality of fluidic port connections 1182, 183, 184, 1185 186, 187 for coupling fluid accessories with the surgical fluidics cassette 150. Illuminating the various port connections on the surgical fluidics cassette 150 would help assist a user in setting up the fluidic accessories properly. For example, the graphical user interface (GUI) on the monitor 110 of the surgical console 100 can be used to display the steps for setting up the fluidics connections and the various ports on the cassette can be illuminated to specifically illustrate which port relates to the displayed step. However, as noted above, the additional illumination should not introduce light in an areas of the sensors that would interfere with the detection of fluid levels and pressure.

In some embodiments of the present technology, a fluidic port illumination light source is arranged within the cassette receiver. Also, the surgical fluidics cassette includes an opaque substrate that includes a plurality of light pipes connecting a transmissive optical interface with a plurality of transmissive portions each at least partially surrounding one of the plurality of fluidic port connections. In these cases, the opaque substrate prevents a fluidic port illumination light from the fluidic port illumination light source from interfering with the light-sensitive fluid level detection system when the surgical fluidics cassette is coupled with the cassette receiver. Also, the transmissive optical interface, the plurality of light pipes, and the transmissive portions on the opaque substrate allow the fluidic port illumination light to illuminate the transmissive portions of the opaque substrate and annunciate the plurality of fluidic port connections.

Figure 5A:
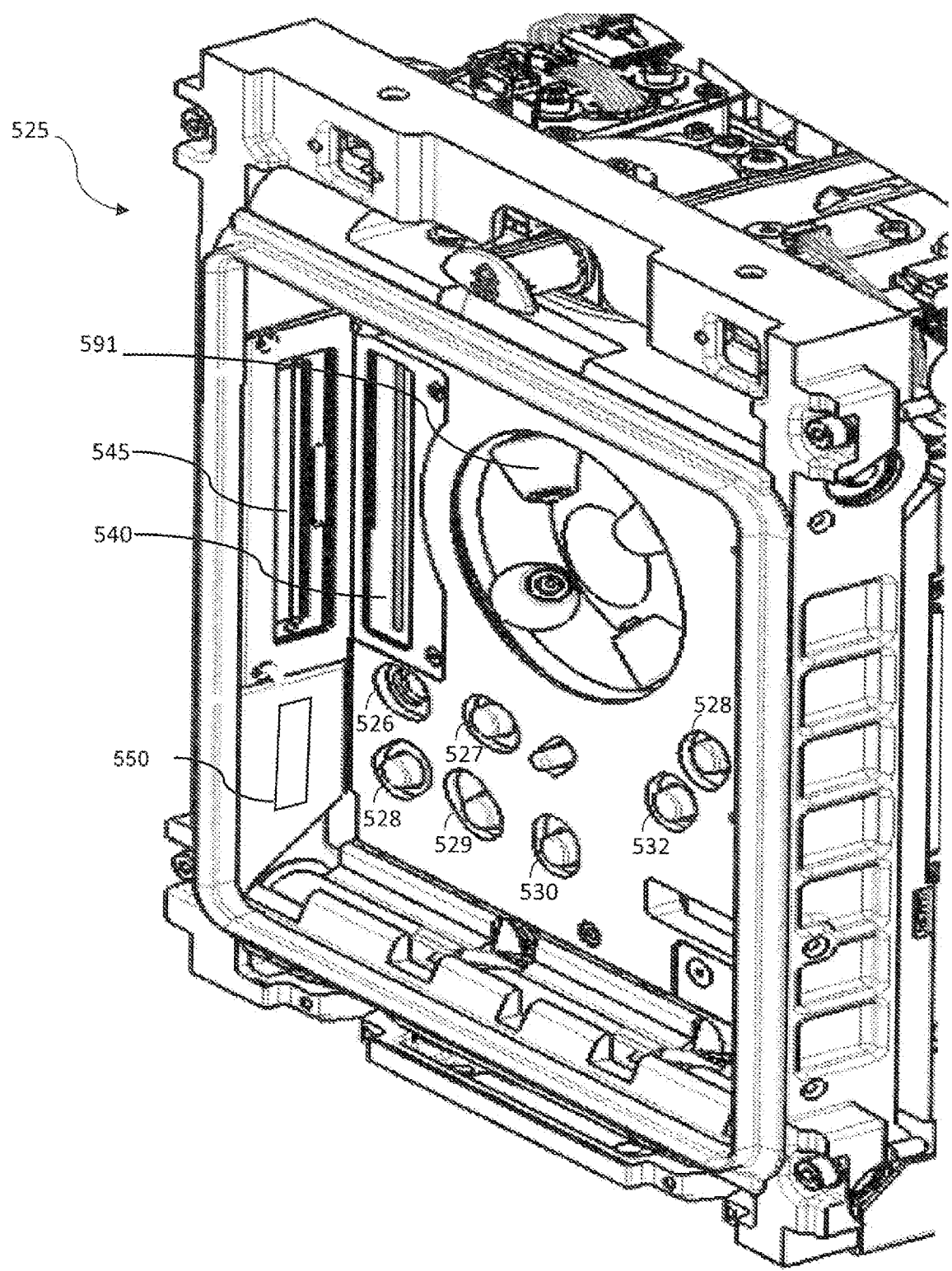
FIG. 5A illustrates a cassette receiver according to a particular embodiment of the present disclosure, without a surgical fluidics cassette inserted.

FIG. 5A illustrates a cassette receiver 525 according to some embodiments of the present technology, without a surgical fluidics cassette inserted. The cassette receiver 525 can have various pneumatic input and output ports 526, 527, 528, 529, 530, 531, 532 to interface with the surgical fluidics cassette and can further include an opening to allow peristaltic pump rollers 591 to contact the surgical fluidics cassette during operation. Also, the cassette receiver 525 can include a fluid detection system including one or more light source 540 to project light into the walls of the cassette chambers and one or more sensor array 545 to detect the light refracted through the chamber (or reflected from the chamber wall). Additionally, the cassette receiver 525 can include a fluidic port illumination light source 550 for providing illumination to the fluidic port connections on the surface of a cassette receiver 525 without interfering with the fluid detection system.

Figure 5B:
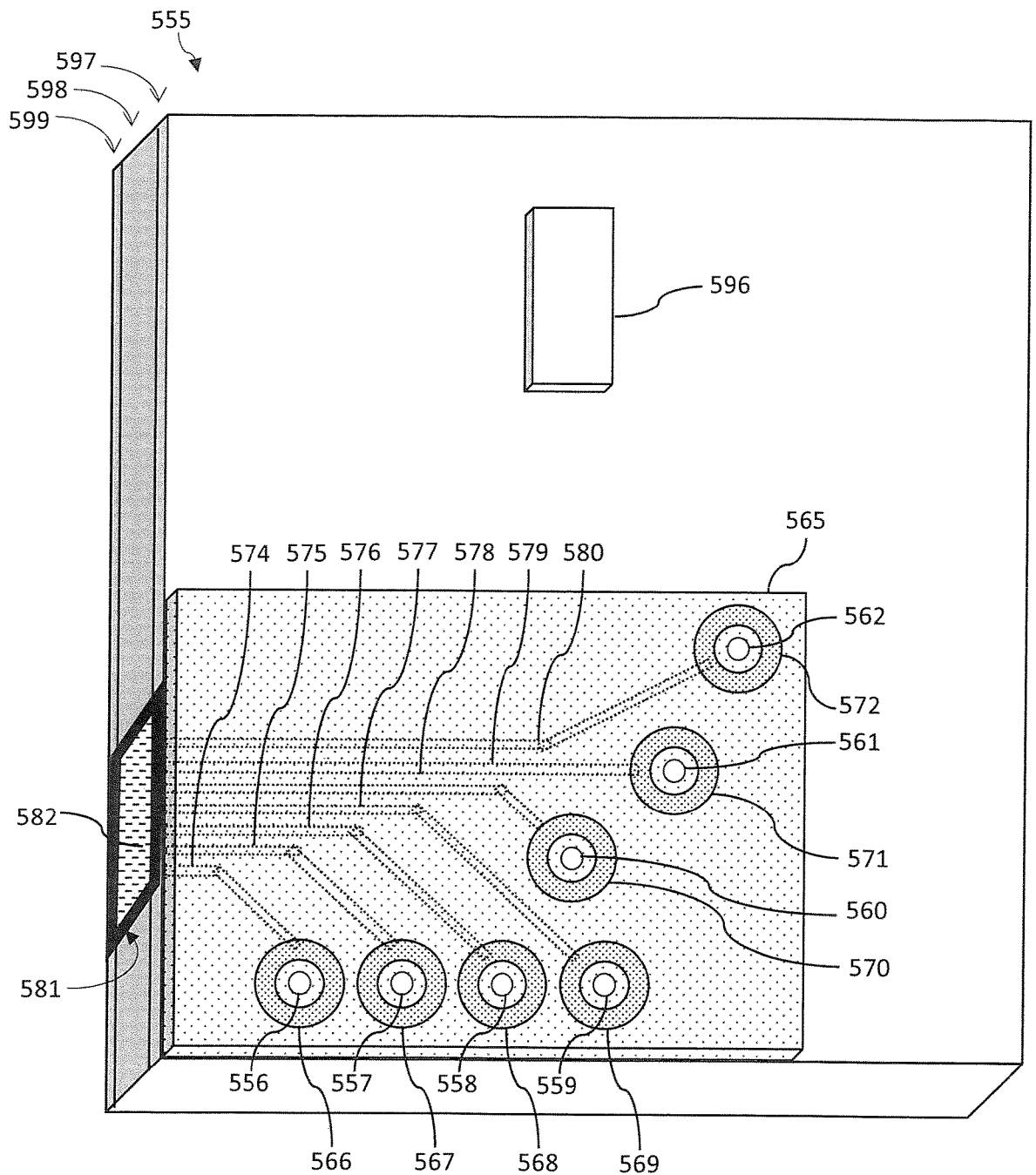
FIG. 5B illustrates a surgical fluidics cassette, according to a particular embodiment of the present disclosure, with light pipes being arranged to illuminate a group of fluidic port connections in the cover plate of the surgical fluidics cassette.

FIG. 5B illustrates a surgical fluidics cassette 555 according to some embodiments of the present technology, with a group of fluidic port connections 556, 557, 558, 559, 560, 561, 562 in the cover plate 597 of the surgical fluidics cassette 555. Surgical fluidics cassette 555 is configured to be received by cassette receiver 525 (FIG. 5A). Surgical fluidics cassette 555 includes a surgical console interface section 599, a middle section 598, and a handle 596. Surgical fluidics cassette 555 also includes an opaque frame 581 that surrounds an optically transmissive interface 582 on the side of the surgical fluidics cassette 555. The opaque frame 581 is arranged on the surgical cassette 555 such that, when the surgical cassette 555 is coupled with the cassette receiver 525, the opaque frame 581 aligns with the fluidic port illumination light source 550 and blocks light from the fluidic port illumination light source 550, except into the optically transmissive interface 582. The opaque frame 581 effectively prevents a fluidic port illumination light from the fluidic port illumination light source 550 from interfering with the fluid level detection system, e.g. the one or more sensor array 545 in the cassette receiver 525.

The surgical fluidics cassette 555 also includes an opaque substrate 565 attached to the cover plate 597. The opaque substrate 565 includes optically transmissive interface portions 566, 567, 568, 569, 570, 571, 572 of the opaque substrate 565. The transmissive interface portions 566, 567, 568, 569, 570, 571, 572 include an interface to the fluidic port connections 556, 557, 558, 559, 560, 561, 562 and include an optically transmissive material on the surface of the opaque substrate 565 at least partially surrounding the fluidic port connections 556, 557, 558, 559, 560, 561, 562.

The opaque substrate 565 contains light pipes 574, 575, 576, 577, 578, 579, 580 that are optically isolated from one another. In some cases, the opaque frame 581 and the opaque substrate 565 are integrally formed.

The distal end of the light pipes 574, 575, 576, 577, 578, 579, 580 are optically coupled with the optically transmissive interface portions 566, 567, 568, 569, 570, 571, 572 of the opaque substrate 565. Additionally, the proximal end of the light pipes 574, 575, 576, 577, 578, 579, 580 are optically coupled with the optically transmissive interface 582 of the opaque frame 581.

The fluidic port illumination light source 550 can provide illumination to one or more of the light pipes 574, 575, 576, 577, 578, 579, 580 via the optically transmissive interface 582. The light pipes 574, 575, 576, 577, 578, 579, 580 receiving illumination deliver the illumination to a respective optically transmissive interface portions 566, 567, 568, 569, 570, 571, 572, thereby providing illumination around the fluidic port connections 556, 557, 558, 559, 560, 561, 562.

As explained above, the ophthalmic surgical console 100 includes a monitor 110 and a processor (not shown) for displaying a graphical user interface (GUI) on the monitor 110. The GUI can include visual instructions for connecting one or more fluidic accessories to the one or more of the plurality of fluidic port connections 556, 557, 558, 559, 560, 561, 562 on the cassette 555. In some cases, the fluidic port illumination light source 550 can be controlled to selectively illuminate one or more of the light pipes 574, 575, 576, 577, 578, 579, 580 to illuminate its respective optically transmissive interface portions 566, 567, 568, 569, 570, 571, 572 in a manner that is consistent with the visual instructions on the GUI. In some cases, the fluidic port illumination light source 550 is an array of light sources with each light source in the array is surrounded with opaque cladding and aligned with an individual light pipe when the surgical fluidics cassette 555 is coupled with the cassette receiver 525. Additionally, the individual light sources can also vary in color (e.g. field programmable LEDs) and the visual instructions can be color-coded. In some cases, the fluidic port illumination light source 550 is an aiming illumination source that can be controlled to selectively aim illumination to the proximal ends of one or more of the plurality of light pipes.

Figure 6:
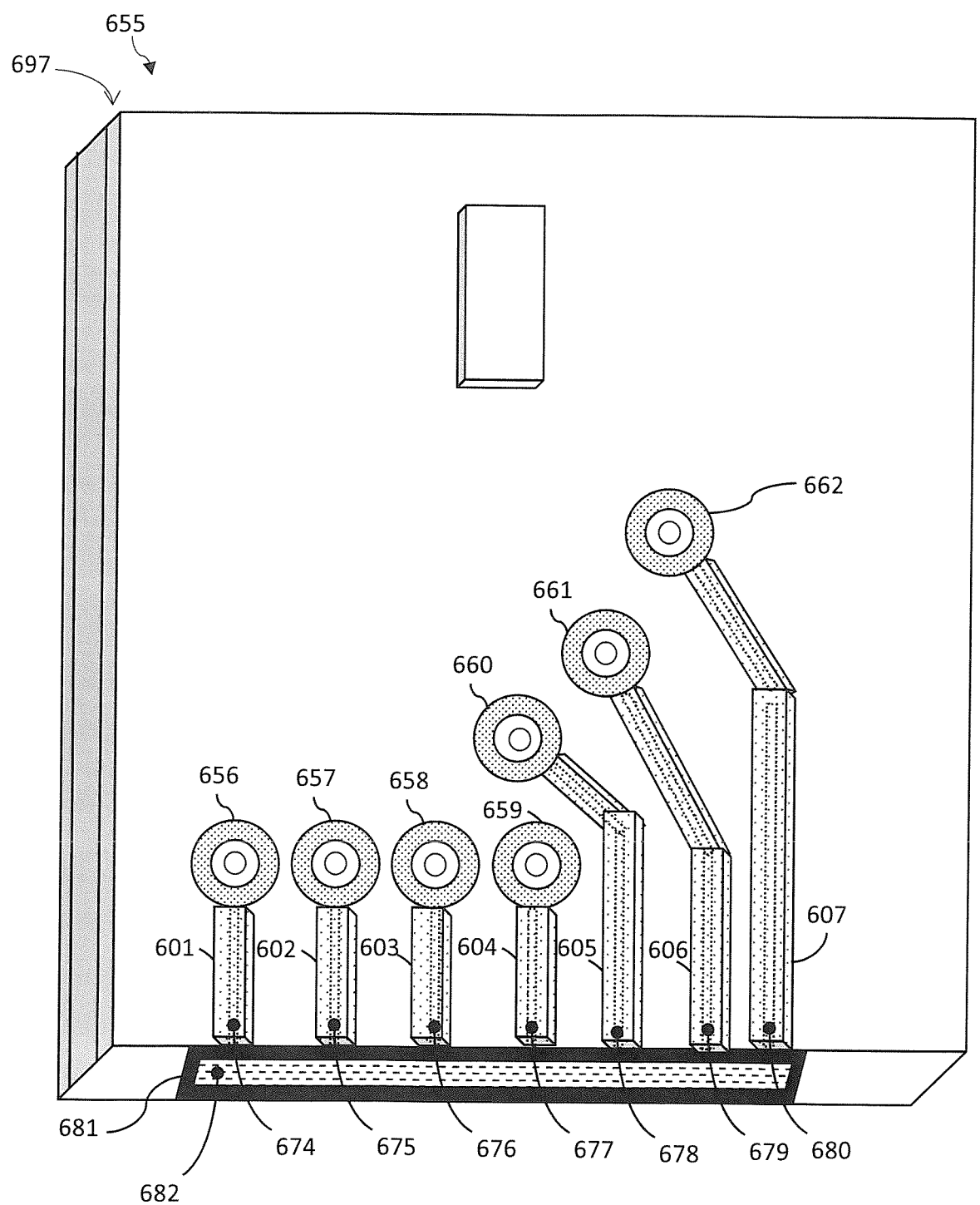
FIG. 6 illustrates another surgical fluidics cassette, according to a particular embodiment of the present disclosure, with light pipes being arranged to illuminate a group of fluidic port connections in the cover plate of the surgical fluidics cassette.

FIG. 6 illustrates a surgical fluidics cassette 655, according to another embodiment, with light pipes 674, 675, 676, 677, 678, 679, 680 being arranged to illuminate a group of fluidic port connections 656, 657, 658, 659, 660, 661, 662 in the cover plate 697 of the surgical cassette 655.

Here, the surgical fluidics cassette 655 includes an opaque frame 681 that surrounds an optically transmissive interface 682 on the bottom of the surgical fluidics cassette 655 and the opaque frame 681 aligns with a fluidic port illumination light source arranged in the bottom of a cassette receiver, preventing a fluidic port illumination light from the fluidic port illumination light source from interfering with the fluid level detection system. The surgical fluidics cassette 655 also includes a plurality of opaque ridges 601, 602, 603, 604, 605, 606, and 607 attached to the cover plate 697 and containing the light pipes 674, 675, 676, 677, 678, 679, 680, respectively.

Figure 7A:
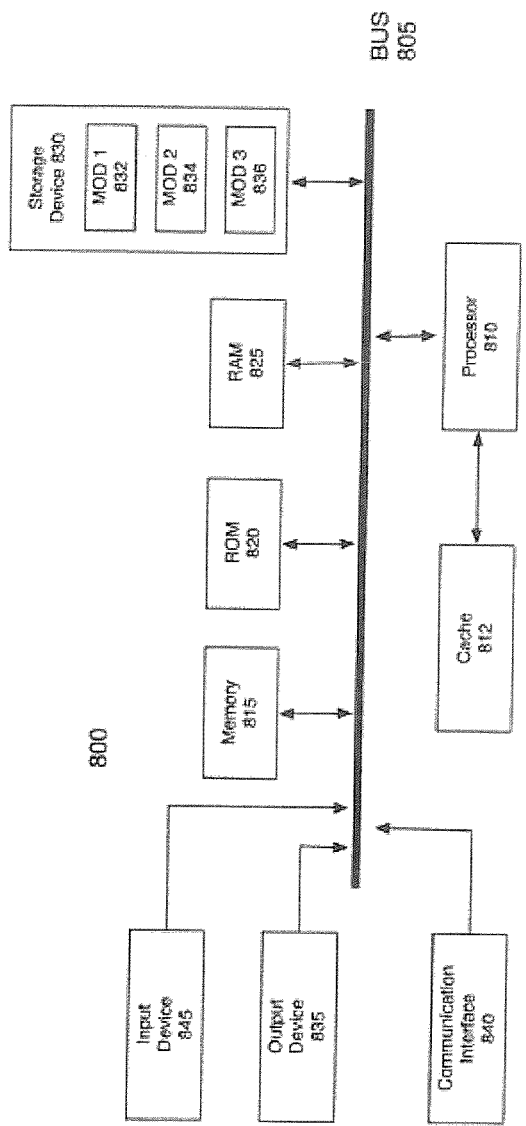
FIG. 7A and FIG. 7B illustrate computer system architectures for controlling surgical consoles according to particular embodiments of the present disclosure.
Figure 7B:
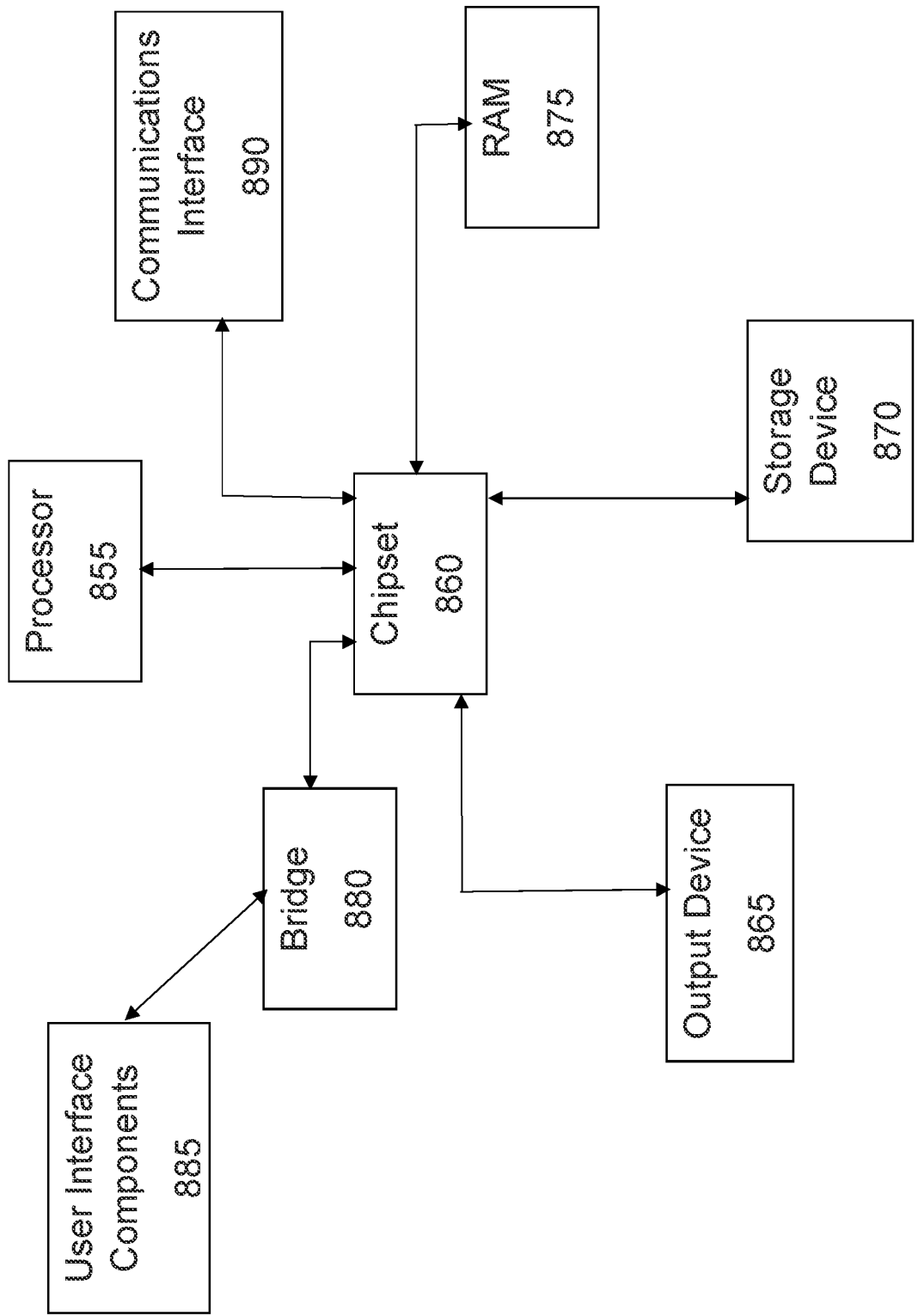

FIG. 7A and FIG. 7B illustrate exemplary possible system embodiments. The more appropriate embodiment will be apparent to those of ordinary skill in the art when practicing the present technology. Persons of ordinary skill in the art will also readily appreciate that other system embodiments are possible.

FIG. 7A illustrates a conventional system bus computing system architecture 800 wherein the components of the system are in electrical communication with each other using a bus 805. Exemplary system 800 includes a processing unit (CPU or processor) 810 and a system bus 805 that couples various system components including the system memory 815, such as read only memory (ROM) 820 and random access memory (RAM) 825, to the processor 810. The system 800 can include a cache of high-speed memory connected directly with, in close proximity to, or integrated as part of the processor 810. The system 800 can copy data from the memory 815 and/or the storage device 830 to the cache 812 for quick access by the processor 810. In this way, the cache can provide a performance boost that avoids processor 810 delays while waiting for data. These and other modules can control or be configured to control the processor 810 to perform various actions. Other system memory 815 may be available for use as well. The memory 815 can include multiple different types of memory with different performance characteristics. The processor 810 can include any general purpose processor and a hardware module or software module, such as module 832, module 834, and module 836 stored in storage device 830, configured to control the processor 810 as well as a special-purpose processor where software instructions are incorporated into the actual processor design. The processor 810 may essentially be a completely self-contained computing system, containing multiple cores or processors, a bus, memory controller, cache, etc. A multi-core processor may be symmetric or asymmetric.

To enable user interaction with the computing device 500, an input device 845 can represent any number of input mechanisms, such as a microphone for speech, a touch-sensitive screen for gesture or graphical input, keyboard, mouse, motion input, speech and so forth. An output device 835 can also be one or more of a number of output mechanisms known to those of skill in the art. In some instances, multimodal systems can enable a user to provide multiple types of input to communicate with the computing device 800. The communications interface 840 can generally govern and manage the user input and system output. There is no restriction on operating on any particular hardware arrangement and therefore the basic features here may easily be substituted for improved hardware or firmware arrangements as they are developed.

Storage device 830 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 825, read only memory (ROM) 820, and hybrids thereof.

The storage device 830 can include software modules 832, 834, 836 for controlling the processor 810. Other hardware or software modules are contemplated. The storage device 830 can be connected to the system bus 805. In one aspect, a hardware module that performs a particular function can include the software component stored in a computer-readable medium in connection with the necessary hardware components, such as the processor 810, bus 805, display 835, and so forth, to carry out the function.

FIG. 7B illustrates a computer system 850 having a chipset architecture that can be used in executing the described method and generating and displaying a graphical user interface (GUI). Computer system 850 is an example of computer hardware, software, and firmware that can be used to implement the disclosed technology. System 850 can include a processor 855, representative of any number of physically and/or logically distinct resources capable of executing software, firmware, and hardware configured to perform identified computations. Processor 855 can communicate with a chipset 860 that can control input to and output from processor 855. In this example, chipset 860 outputs information to output 865, such as a display, and can read and write information to storage device 870, which can include magnetic media, and solid state media, for example. Chipset 860 can also read data from and write data to RAM 875. A bridge 880 for interfacing with a variety of user interface components 885 can be provided for interfacing with chipset 860. Such user interface components 885 can include a keyboard, a microphone, touch detection and processing circuitry, a pointing device, such as a mouse, and so on. In general, inputs to system 850 can come from any of a variety of sources, machine generated and/or human generated.

Chipset 860 can also interface with one or more communication interfaces 890 that can have different physical interfaces. Such communication interfaces can include interfaces for wired and wireless local area networks, for broadband wireless networks, as well as personal area networks. Some applications of the methods for generating, displaying, and using the GUI disclosed herein can include receiving ordered datasets over the physical interface or be generated by the machine itself by processor 855 analyzing data stored in storage 870 or 875. Further, the machine can receive inputs from a user via user interface components 885 and execute appropriate functions, such as browsing functions by interpreting these inputs using processor 855.

It can be appreciated that exemplary systems 800 and 850 can have more than one processor 810 or be part of a group or cluster of computing devices networked together to provide greater processing capability.

For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A surgical console comprising:
   a processor;
   a display;
   a cassette receiver configured to couple with a surgical fluidics cassette, the cassette receiver including:
      a fluid level detection system including one or more light sources coupled with the processor and one or more sensors coupled with the processor, the fluid detection system arranged to detect a fluid level in one or more chambers of the surgical fluidics cassette coupled with the cassette receiver;
      a fluidic port illumination light source arranged within the cassette receiver such that, when the surgical fluidics cassette is coupled with the cassette receiver, the fluidic port illumination light source interfaces with a transmissive optical interface surrounded by an opaque frame on the surgical fluidics cassette, wherein the opaque frame prevents a fluidic port illumination light from the fluidic port illumination light source from interfering with the fluid level detection system, and wherein the transmissive optical interface allows the fluidic port illumination light to transmit into a proximal end of one or more of a plurality of light pipes in an opaque substrate on the surgical fluidics cassette;
   a controller; and
   a non-transitory computer-readable medium containing instructions which, when executed by the processor, cause the controller to selectively cause the fluidic port illumination light source to provide illumination to the transmissive optical interface of the surgical fluidics cassette and to the proximal end of the one or more of a plurality of light pipes in the opaque substrate of the surgical fluidics cassette, thereby illuminating one or more of a plurality of transmissive interface portions at a distal end of each of the plurality of light pipes, wherein each of the transmissive interface portions at least partially surrounds one of a plurality of fluidic port connections on a cover plate of the surgical fluidics cassette.

2. The surgical console of claim 1, further comprising a display,
   wherein the non-transitory computer-readable medium contains further instructions which, when executed by the processor, cause the display to display a graphical user interface (GUI) including visual instructions for connecting one or more fluidic accessories to the one or more of the plurality of fluidic port connections on the surgical fluidics cassette.

3. The surgical console of claim 2, wherein the fluidic port illumination light source includes an array of illumination sources with each illumination source in the array of illumination sources being aligned with the proximal end of one of the plurality of light pipes on the opaque substrate.

4. The surgical console of claim 3, wherein the non-transitory computer-readable medium contains further instructions which, when executed by the processor, cause the controller to selectively activate, consistent with the visual instructions on the GUI, one or more of the illumination sources in the array of illumination sources, thereby causing one or more of the plurality of transmissive interface portions to transmit illumination an annunciating one or more of the fluidic port connections as being consistent with the visual instructions on the GUI.

5. The surgical console of claim 4, wherein the array of illumination sources includes varying colored illumination sources, and wherein the visual instructions on the GUI include color-coded instructions for attaching color-coded fluidic accessory connections to the plurality of fluidic port connections on a cover plate of the surgical fluidics cassette.

6. The surgical console of claim 1, wherein the fluidic port illumination light source includes an aiming light source, the aiming light source configured to be aimed at the proximal end of each of the one of the plurality of light pipes on the opaque substrate.

7. The surgical console of claim 6, wherein the non-transitory computer-readable medium contains further instructions which, when executed by the processor, cause the controller to selectively aim, consistent with the visual instructions on the GUI, the aiming illumination source at the transmissive optical interface of the surgical fluidics cassette and to the proximal end of one or more of the plurality of light pipes, thereby causing one or more of the plurality of transmissive interface portions to transmit illumination and annunciating one or more of the fluidic port connections as being consistent with the visual instructions on the GUI.

8. The surgical console of claim 1, wherein the opaque frame and the opaque substrate are integrally formed.

* * * * *